(12) United States Patent
Paul et al.

(10) Patent No.: US 8,222,908 B2
(45) Date of Patent: Jul. 17, 2012

(54) CAPACITIVE DETECTOR FOR USE IN EXTRUSION-BASED DIGITAL MANUFACTURING SYSTEMS

(75) Inventors: Thomas P. Paul, Eden Prairie, MN (US); J. Samuel Batchelder, Somers, NY (US)

(73) Assignee: Stratasys, Inc., Eden Prairie, MN (US)

( * ) Notice: Subject to any disclaimer, the term of this patent is extended or adjusted under 35 U.S.C. 154(b) by 404 days.

(21) Appl. No.: 12/706,095

(22) Filed: Feb. 16, 2010

(65) Prior Publication Data

US 2011/0199104 A1  Aug. 18, 2011

(51) Int. Cl.
*G01R 27/26*  (2006.01)

(52) U.S. Cl. .......... 324/679; 425/375; 425/169; 264/28; 264/308; 324/671; 324/686

(58) Field of Classification Search .................... 324/679
See application file for complete search history.

(56) References Cited

U.S. PATENT DOCUMENTS

| | | | |
|---|---|---|---|
| 3,027,266 A | 3/1962 | Wikne | |
| 4,296,517 A | 10/1981 | Bohler et al. | |
| 4,640,608 A | 2/1987 | Higaya et al. | |
| 5,121,329 A * | 6/1992 | Crump | 700/119 |
| 5,340,433 A * | 8/1994 | Crump | 156/578 |
| 5,503,785 A | 4/1996 | Crump et al. | |
| 5,594,652 A | 1/1997 | Penn et al. | |
| 5,764,521 A | 6/1998 | Batchelder et al. | |
| 5,866,058 A | 2/1999 | Batchelder et al. | |
| 5,939,008 A | 8/1999 | Comb et al. | |
| 5,968,561 A * | 10/1999 | Batchelder et al. | 425/375 |
| 6,004,124 A * | 12/1999 | Swanson et al. | 425/375 |
| 6,007,318 A | 12/1999 | Russell et al. | |
| 6,022,207 A | 2/2000 | Dahlin et al. | |
| 6,028,410 A | 2/2000 | Leavitt et al. | |
| 6,054,077 A * | 4/2000 | Comb et al. | 264/40.7 |
| 6,067,480 A | 5/2000 | Stuffle et al. | |
| 6,070,107 A | 5/2000 | Lombardi et al. | |
| 6,085,957 A * | 7/2000 | Zinniel et al. | 226/8 |
| 6,175,422 B1 | 1/2001 | Penn et al. | |
| 6,193,923 B1 | 2/2001 | Leyden et al. | |
| 6,228,923 B1 | 5/2001 | Lombardi et al. | |
| 6,238,613 B1 * | 5/2001 | Batchelder et al. | 264/404 |
| 6,270,335 B2 | 8/2001 | Leyden et al. | |
| 6,305,769 B1 | 10/2001 | Thayer et al. | |
| 6,375,874 B1 * | 4/2002 | Russell et al. | 264/28 |
| 6,391,251 B1 | 5/2002 | Keicher et al. | |
| 6,490,496 B1 | 12/2002 | Dacey | |
| 6,508,971 B2 | 1/2003 | Leyden et al. | |
| 6,532,394 B1 | 3/2003 | Earl et al. | |
| 6,572,807 B1 | 6/2003 | Fong | |
| 6,629,011 B1 | 9/2003 | Calderon et al. | |
| 6,685,866 B2 * | 2/2004 | Swanson et al. | 264/308 |
| 6,722,872 B1 * | 4/2004 | Swanson et al. | 425/225 |
| 6,749,414 B1 | 6/2004 | Hanson et al. | |
| 6,776,602 B2 | 8/2004 | Swanson et al. | |
| 6,790,403 B1 | 9/2004 | Priedeman, Jr. et al. | |

(Continued)

*Primary Examiner* — Timothy J Dole
*Assistant Examiner* — Benjamin M Baldridge
(74) *Attorney, Agent, or Firm* — Brian R. Morrison; Westman, Champlin & Kelly, P.A.

(57) ABSTRACT

A detector for use in an extrusion-based digital manufacturing system, the detector comprising a sense conductive component and an excitation conductive component to define a first gap that is configured to receive a consumable material used in the extrusion-based digital manufacturing system, where the excitation conductive component is configured to generate a first electrical field across the first gap.

19 Claims, 9 Drawing Sheets

U.S. PATENT DOCUMENTS

| | | |
|---|---|---|
| 6,907,307 B2 * | 6/2005 | Chen et al. .................... 700/119 |
| 6,923,634 B2 * | 8/2005 | Swanson et al. ............. 425/169 |
| 6,936,212 B1 | 8/2005 | Crawford |
| 6,989,115 B2 | 1/2006 | Russell et al. |
| 7,086,280 B2 * | 8/2006 | Wakeman et al. ........... 73/61.61 |
| 7,122,246 B2 | 10/2006 | Comb et al. |
| 7,384,255 B2 | 6/2008 | LaBossiere et al. |
| 7,604,470 B2 | 10/2009 | LaBossiere et al. |
| 7,625,200 B2 | 12/2009 | Leavitt |
| 2002/0067174 A1 * | 6/2002 | McAllister .................... 324/690 |
| 2002/0118025 A1 * | 8/2002 | Yamagishi et al. ........... 324/672 |
| 2002/0195747 A1 * | 12/2002 | Hull et al. .................... 264/401 |
| 2003/0076371 A1 | 4/2003 | Fong |
| 2003/0184318 A1 * | 10/2003 | Lenormand et al. .......... 324/663 |
| 2008/0076190 A1 * | 3/2008 | Carlisle et al. ................ 436/536 |
| 2008/0191717 A1 * | 8/2008 | Gundlach et al. ............. 324/686 |
| 2008/0213419 A1 | 9/2008 | Skubic et al. |
| 2008/0317894 A1 | 12/2008 | Turley et al. |
| 2009/0263582 A1 | 10/2009 | Batchelder |
| 2010/0021580 A1 | 1/2010 | Swanson et al. |
| 2010/0096072 A1 * | 4/2010 | Hopkins et al. ............... 156/155 |
| 2010/0096485 A1 * | 4/2010 | Taatjes et al. ................. 242/171 |
| 2010/0096489 A1 | 4/2010 | Taatjes et al. |
| 2010/0141274 A1 * | 6/2010 | Keller et al. .................. 324/671 |

* cited by examiner

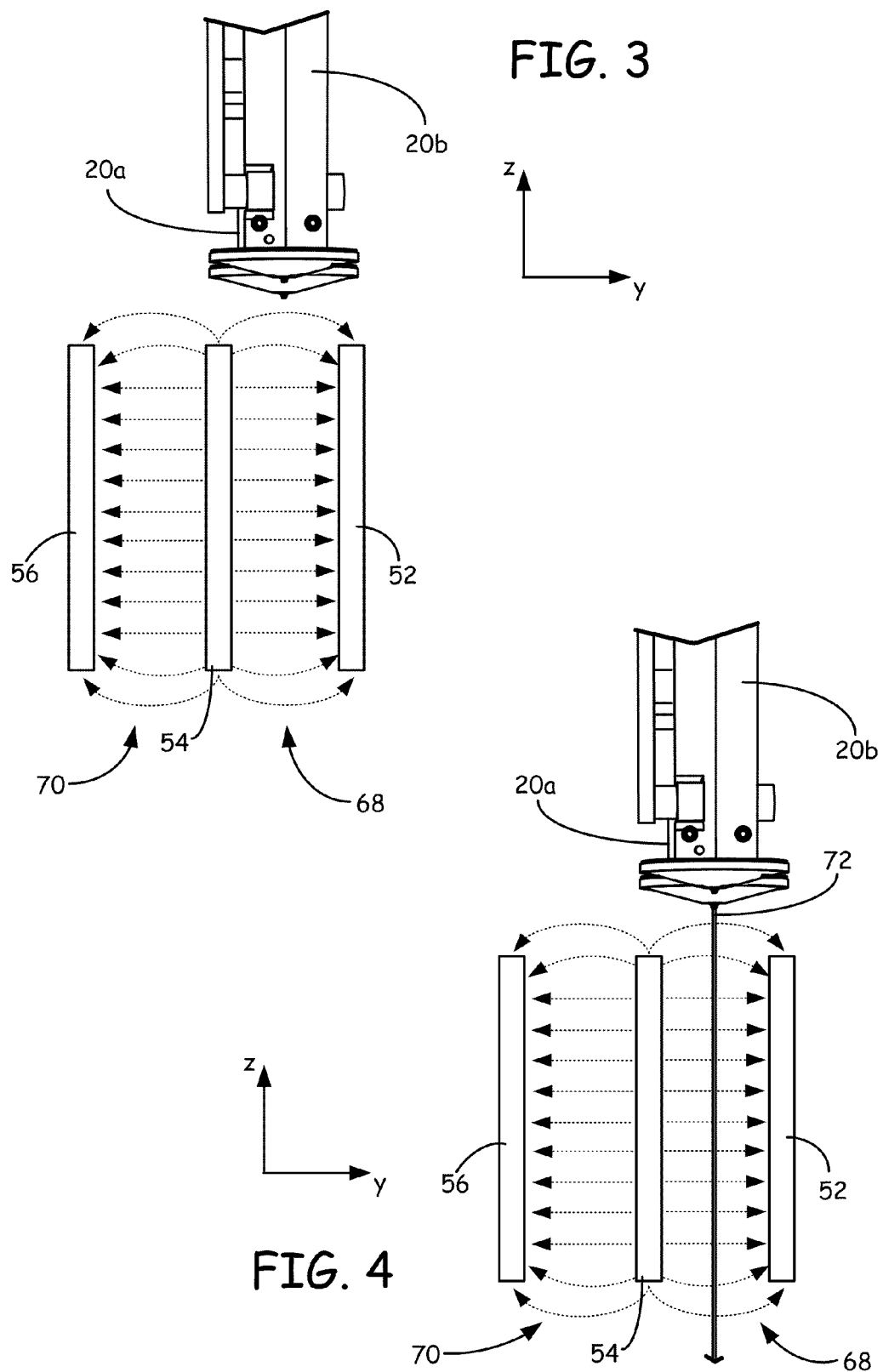

CAPACITIVE DETECTOR FOR USE IN EXTRUSION-BASED DIGITAL MANUFACTURING SYSTEMS

BACKGROUND

The present disclosure relates to direct digital manufacturing systems for building three-dimensional (3D) models with layer-based additive techniques. In particular, the present disclosure relates to devices for detecting consumable materials, such as modeling and support materials, used in extrusion-based digital manufacturing systems.

An extrusion-based digital manufacturing system (e.g., fused deposition modeling systems developed by Stratasys, Inc., Eden Prairie, Minn.) is used to build a 3D model from a digital representation of the 3D model in a layer-by-layer manner by extruding a flowable consumable modeling material. The modeling material is extruded through an extrusion tip carried by an extrusion head, and is deposited as a sequence of roads on a substrate in an x-y plane. The extruded modeling material fuses to previously deposited modeling material, and solidifies upon a drop in temperature. The position of the extrusion head relative to the substrate is then incremented along a z-axis (perpendicular to the x-y plane), and the process is then repeated to form a 3D model resembling the digital representation.

Movement of the extrusion head with respect to the substrate is performed under computer control, in accordance with build data that represents the 3D model. The build data is obtained by initially slicing the digital representation of the 3D model into multiple horizontally sliced layers. Then, for each sliced layer, the host computer generates a build path for depositing roads of modeling material to form the 3D model.

In fabricating 3D models by depositing layers of a modeling material, supporting layers or structures are typically built underneath overhanging portions or in cavities of objects under construction, which are not supported by the modeling material itself. A support structure may be built utilizing the same deposition techniques by which the modeling material is deposited. The host computer generates additional geometry acting as a support structure for the overhanging or free-space segments of the 3D model being formed. Consumable support material is then deposited from a second nozzle pursuant to the generated geometry during the build process. The support material adheres to the modeling material during fabrication, and is removable from the completed 3D model when the build process is complete.

SUMMARY

An aspect of the present disclosure is directed to a detector for use in an extrusion-based digital manufacturing system. The detector includes a control board configured to be retained in the extrusion-based digital manufacturing system, and a sense conductive component. The detector also includes an excitation conductive component that defines a first gap with the sense conductive component, where the first gap is configured to receive a consumable material used in the extrusion-based digital manufacturing system. The excitation conductive component is configured to generate a first electrical field across the first gap.

In some embodiments, the detector may also include a reference conductive component, where the excitation conductive component is disposed between the sense conductive component and the reference conductive component. In these embodiments, the excitation conductive component and the reference conductive component define a second gap, and the excitation conductive component may also be configured to generate a second electrical field across the second gap.

Another aspect of the present disclosure is directed to a detector for use in an extrusion-based digital manufacturing system, where the detector includes an excitation conductive component, a sense conductive component, and a biasing component configured to engage a consumable material with the excitation conductive component and the reference conductive component. The excitation conductive component is configured to generate an electrical field with the sense conductive component. The detector also includes a processor configured to compare capacitive values of sampled signals operably received from the sense conductive component to predetermined capacitive values to identify at least one compositional property of the consumable material.

Another aspect of the present disclosure is directed to a method for detecting a consumable material in an extrusion-based digital manufacturing system. The method includes generating a first electrical field between an excitation conductive component and a sense conductive component, and generating a second electrical field between the excitation conductive component and a reference conductive component. The method also includes introducing the consumable material between the excitation conductive component and the sense conductive component while the first and second electrical fields are generated, and operably sampling capacitive values of the first and second electrical fields while the consumable material is introduced between the excitation conductive component and the sense conductive component. The method further includes performing at least one computational analysis on the sampled capacitive values to identify the presence of the consumable material between the excitation conductive component and the sense conductive component.

BRIEF DESCRIPTION OF THE DRAWINGS

FIG. 3 is an expanded view of the extrusion head in use with the first embodied capacitive detector, where a consumable material extrudate from the extrusion head is not present.

FIG. 4 is an expanded view of the extrusion head in use with the first embodied capacitive detector, where the consumable material extrudate from the extrusion head is present.

DETAILED DESCRIPTION

The present disclosure is directed capacitive detectors for detecting the presence of materials used in direct digital manufacturing systems, such as extrusion-based digital manufacturing systems. In a first embodiment, the capacitive detector is located at a purge receptacle and is configured to detect the presence of extrudates from an extrusion head during liquefier purges. In this embodiment, detecting the presence of the extrudates at the purge receptacle may identify when a loss of extrusion event occurs (e.g., a clogged extrusion tip).

In a second embodiment, the capacitive detector is located between a supply source of a consumable material and the extrusion head, and is configured to detect the presence of consumable materials (e.g., modeling and support materials) being fed to the extrusion head. In this embodiment, the capacitive detector may also be used to determine one or more compositional properties of the consumable materials, such as moisture concentrations in the consumable materials.

Extrudate Purge Detector

Figure 1:
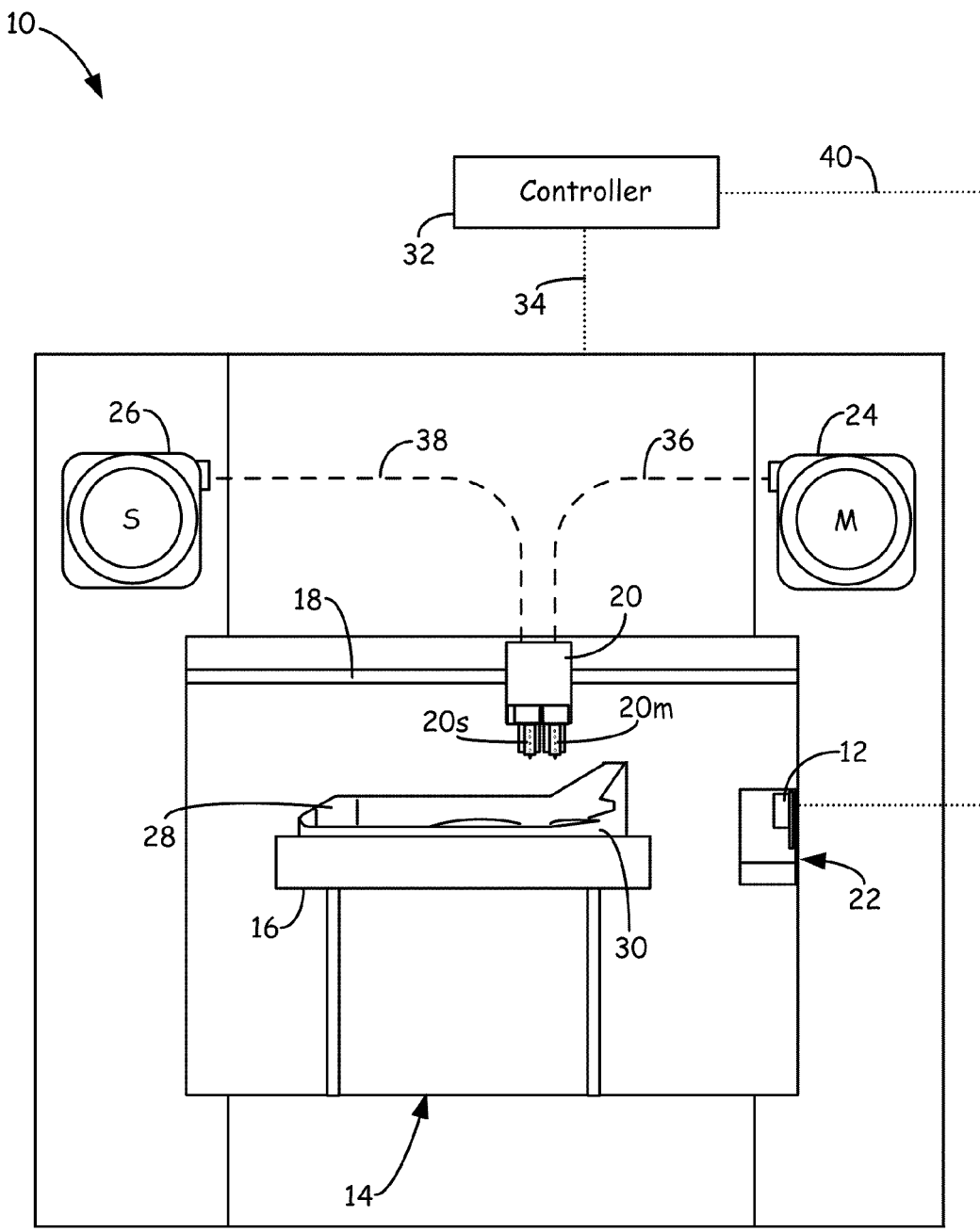
FIG. 1 is a schematic illustration of an extrusion-based digital manufacturing system that includes a capacitive detector of a first embodiment of the present disclosure.

FIG. 1 is a schematic illustration of system 10, which is an extrusion-based digital manufacturing system that includes detector 12. As discussed below, detector 12 is a capacitive detector of the first embodiment of the present disclosure for detecting the presence of extrudates during purge operations. Suitable extrusion-based digital manufacturing systems for system 10 include fused deposition modeling systems developed by Stratasys, Inc., Eden Prairie, Minn., such as those disclosed in Comb et al., U.S. Pat. No. 5,939,008; Swanson et al., U.S. Pat. Nos. 6,722,872 and 6,776,602; and Taatjes et al, U.S. patent application Ser. Nos. 12/255,808 and 12/255,811; and those commercially available under the trade designations "DIMENSION" and "FORTUS" from Stratasys, Inc., Eden Prairie, Minn.

System 10 includes build chamber 14, platform assembly 16, gantry 18, extrusion head 20, purge receptacle 22, and supply sources 24 and 26. Build chamber 14 is an enclosed environment that contains platform assembly 16, a portion of gantry 18, extrusion head 20, purge receptacle 22, and detector 12. During a build operation, build chamber 14 is desirably heated to reduce the rate at which the modeling and support materials solidify after being extruded and deposited.

Platform assembly 16 is a receiving platform on which a 3D model (referred to as 3D model 28) and a corresponding support structure (referred to as support structure 30) are built, and desirably moves along a vertical z-axis based on signals provided from controller 32. Controller 32 is one or more computer-operated controllers for operating system 10, and may be located internally or externally to system 10. As shown, controller 32 may communicate with build chamber 14, platform assembly 16, gantry 18, and extrusion head 20 over communication line 34. While illustrated as a single signal line, communication line 34 may include one or more signal lines for allowing controller 32 to communicate with various components of system 10, such as build chamber 14, platform assembly 16, gantry 18, and extrusion head 20.

Gantry 18 is a guide rail system that is configured to move extrusion head 20 in a horizontal x-y plane within build chamber 14 based on signals provided from system controller 32. The horizontal x-y plane is a plane defined by an x-axis and a y-axis, where the x-axis, the y-axis, and the z-axis are orthogonal to each other. In an alternative embodiment, platform assembly 16 may be configured to move along two axes within build chamber 14 (e.g., x-z plane or the y-z plane), and extrusion head 20 may be configured to move along a single horizontal axis (e.g., the x-axis or the y-axis). Other similar arrangements may also be used such that one or both of platform assembly 16 and extrusion head 20 are movable relative to each other.

Extrusion head 20 is supported by gantry 18 for building 3D model 28 and support structure 30 on platform assembly 16 in a layer-by-layer manner, based on signals provided from controller 32. Examples of suitable extrusion heads for extrusion head 20 include those disclosed in LaBossiere, et al., U.S. Pat. Nos. 7,384,255 and 7,604,470; and Leavitt, U.S. Pat. No. 7,625,200. Alternatively, system 10 may include one or more two-stage pump assemblies, such as those disclosed in Batchelder et al., U.S. Pat. No. 5,764,521; and Skubic et al., U.S. Patent Application Publication No. 2008/0213419. Furthermore, system 10 may include a plurality of extrusion heads 20 for depositing modeling and/or support materials, such as disclosed in Swanson et al., U.S. patent application Ser. No. 12/180,140.

In the shown embodiment, extrusion head 20 includes a liquefiers 20$m$ and 20$s$, which may be toggled back and forth for selectively extruding modeling and support materials. Accordingly, the modeling material for building 3D model 28 may be fed from supply source 24 to liquefier 20$m$ of extrusion head 20 through pathway 36. Similarly, a support material for building support structure 30 may be fed from supply source 26 to liquefier 20$s$ of extrusion head 20 through pathway 38. System 10 may also include additional drive mechanisms (not shown) configured to assist in feeding the modeling and support materials from supply sources 24 and 26 to extrusion head 20.

Supply sources 24 and 26 are devices for retaining supplies of the modeling and support materials, and which may be loadable to system 10. While illustrated with two supply sources (i.e., supply sources 24 and 26), system 10 may alternatively be configured to feed consumable materials to each liquefier of extrusion head 20 from two or more supply sources to provide for a continuous operation, as disclosed in Swanson et al., U.S. Pat. No. 6,923,634. In some embodiments, the modeling and support materials may be provided to system 10 as filaments. In these embodiments, suitable assemblies (e.g., spooled containers) for supply sources 24 and 26 include those disclosed in Swanson et al., U.S. Pat. No. 6,923,634; Comb et al., U.S. Pat. No. 7,122,246; and Taatjes et al, U.S. patent application Ser. Nos. 12/255,808 and 12/255,811.

Purge receptacle 22 is a container that may be retained in build chamber 14, and is configured to receive extrudates of the modeling and support materials from extrusion head 20 during liquefier purges. As discussed above, detector 12 is a capacitive detector configured to detect the presence of the extrudates from extrusion head 20 during the liquefier purges. As shown, detector 12 may communicate with controller 32 over communication line 40. While illustrated as a single signal line, communication line 40 may also include one or more signal lines for allowing detector 12 to communicate with controller 32 and/or with various components of system 10.

During a build operation, controller 32 directs gantry 18 to move extrusion head 20 around in the horizontal x-y plane within build chamber 14 based on predetermined coordinate patterns. Controller 32 may also direct drive mechanisms (not shown) to selectively feed the modeling and support materials through pathways 36 and 38 to extrusion head 20. Extrusion head 20 thermally melts the successive portions of the received modeling and support materials. The upstream, unmelted portions of the each of the materials may each function as a piston with a viscosity-pump action to extrude the molten material out of its respective liquefier of extrusion head 20. The extruded modeling and support materials may then be deposited onto platform assembly 16 to build 3D model 28 and support structure 30 in a layer-by-layer manner pursuant to the layer-based additive technique.

For each layer, extrusion head 20 may toggle between liquefiers 20$m$ and 20$s$ to selectively deposit the modeling and support materials. Accordingly, when toggled to deposit the modeling material, liquefier 20$m$ is active and liquefier 20$s$ is inactive. Alternatively, when toggled to deposit the support material, liquefier 20$s$ is active and liquefier 20$m$ is inactive. Suitable techniques for toggling liquefiers 20$m$ and 20$s$ between the active and inactive states are disclosed in LaBossiere, et al., U.S. Pat. No. 7,604,470 and Leavitt, U.S. Pat. No. 7,625,200.

A liquefier purge is also desirably performed after each toggling to ready the previously inactive liquefier for use. During each liquefier purge, controller 32 may direct gantry 18 to move extrusion head 20 in the horizontal x-y plane until extrusion head 20 is positioned over purge receptacle 22. Extrusion head 20 may then warm up the active liquefier and extrude the consumable material from the given liquefier into purge receptacle 22 for a short period of time. For example, after forming a layer of support structure 30 (i.e., liquefier 20$s$ is active and liquefier 20$m$ is inactive), extrusion head 20 may be toggled such that liquefier 20$m$ is now active and liquefier 20$s$ is now inactive. Liquefier 20$m$ may then be warmed up and directed to extrude the modeling material into purge receptacle 22 for a short period of time. After the purge operation, liquefier 20$m$ is then ready for use in forming the next layer of 3D model 28.

During a proper liquefier purge, the modeling or support material extrudes respectively from the tip of liquefier 20$m$ or liquefier 20$s$ as an extrudate into purge receptacle 22. However, to attain high resolutions, the tips of liquefiers 20$m$ and 20$s$ desirably have small inner diameters (e.g., from about 250 micrometers (about 10 mils) to about 510 micrometers (about 20 mils)). As such, the modeling or support material residing in the inactive liquefier may potentially solidify at the bottom tip of the given liquefier. This solidification may potentially clog the small-diameter tip of the liquefier, which can prevent the modeling or support material from being deposited the next time it is needed. If not detected, such events can disrupt the build operations, thereby resulting in delays and/or distortions in the resulting 3D model 28 or support structure 30.

The liquefier purges provide suitable points in the build operation to detect tip clogging. In particular, the liquefier purging allows the tip clogging to be detected prior to forming a layer of 3D model 28 or support structure 30. This prevents an unsuccessful extrusion from occurring during the actual layer formation, thereby preserving the dimensional integrities of 3D model 28 and support structure 30. As discussed below, detector 12 is configured to detect the extrudates from liquefiers 20$m$ and 20$s$ during the liquefier purges, thereby allowing system 10 to identify when tip clogging occurs.

Figure 2:
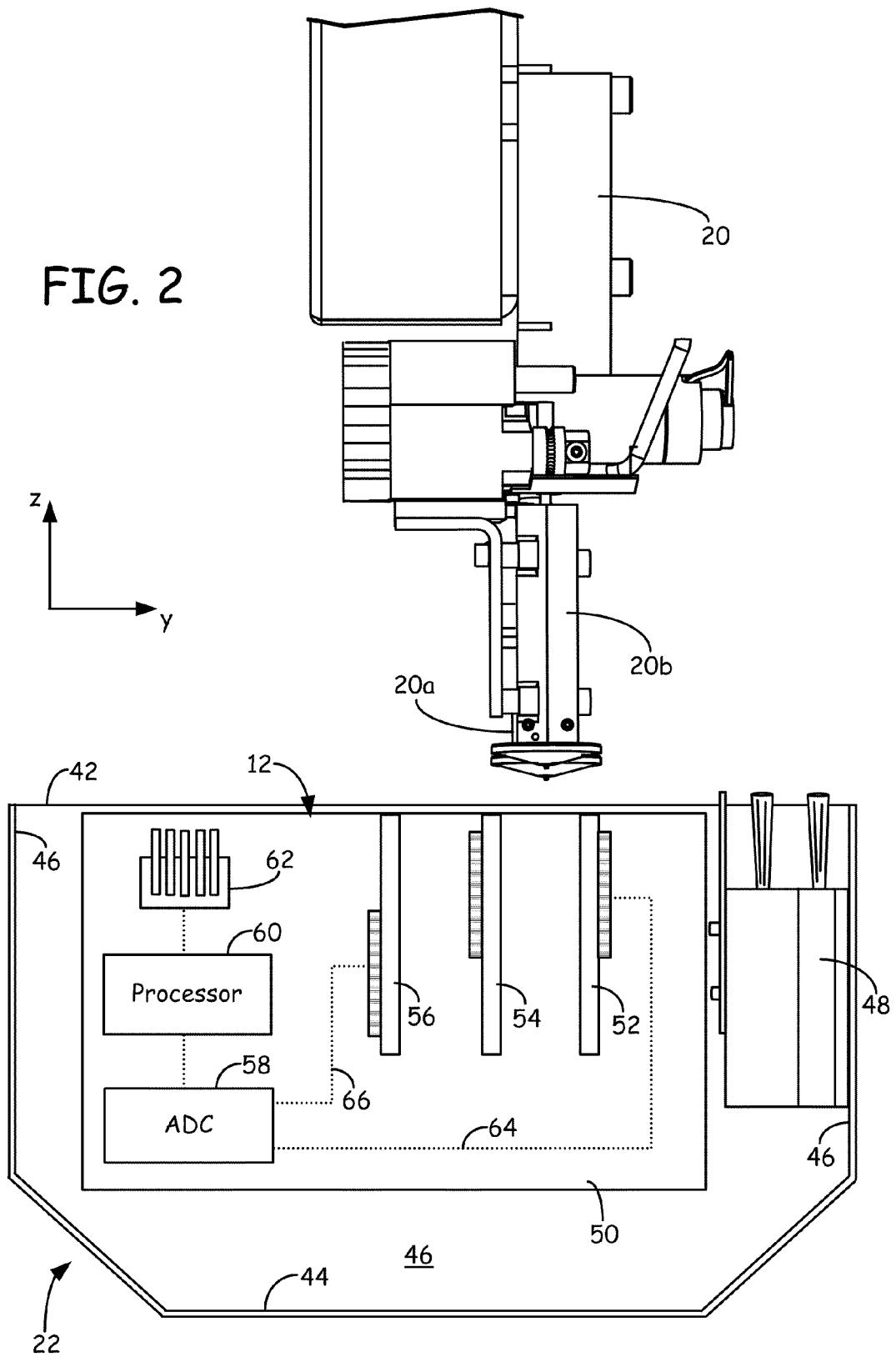
FIG. 2 is a side schematic illustration of an extrusion head of the extrusion-based digital manufacturing system positioned over a purge receptacle of the extrusion-based digital manufacturing system, where the purge receptacle retains the first embodied capacitive detector.

FIG. 2 is a side schematic illustration of extrusion head 20 positioned over purge receptacle 22, where gantry 18 is omitted for ease of discussion. Purge receptacle 22 includes top edge 42, bottom floor 44, and sidewall 46 extending between top edge 42 and bottom floor 44 to form a container having a top opening for collecting purged consumable materials. In alternative embodiments, purge receptacle 22 may exhibit a variety of different designs such that detector 12 is operably secured to at least a portion of sidewall 46, desirably adjacent to top edge 42.

Purge receptacle 22 may also retain tip wipe assembly 48, where tip wipe assembly 48 may also be secured sidewall 46 adjacent to top edge 42. Examples of suitable devices for tip wipe assembly 48 include those disclosed in Swanson, et al., U.S. Pat. No. 6,722,872 and in Turley, et al., U.S. Patent Application Publication No. 2008/0317894.

In the shown embodiment, detector 12 includes circuit board 50, sense plate 52, excitation plate 54, reference plate 56, analog-to-digital converter (ADC) 58, processor 60, and system interface 62. Detector 12 may also include a variety of additional electronic components (not shown) for processing and transmitting capacitance signals. Circuit board 50 is a printed circuit board configured to be operably secured to sidewall 46. Sense plate 52, excitation plate 54, and reference plate 56 are conductive plates operably secured to circuit board 50, and are each desirably connected to a power source (not shown).

As shown, sense plate 52 and excitation plate 54 are offset from each other by a first gap. This arrangement allows sense plate 52 and excitation plate 54 to function as a first parallel-plate capacitor to detect the presence of extrudates deposited between sense plate 52 and excitation plate 54. Correspondingly, excitation plate 54 and reference plate 56 are offset from each other by a second gap. This arrangement also allows excitation plate 54 and reference plate 56 function as a second parallel-plate capacitor to provide baseline capacitance values for the first parallel-plate capacitor. The dual-capacitor design allows detector 12 to compensate for environmental changes, such as changes in temperature and humidity levels. Additionally, as discussed below, the dual-capacitor design also allows extrudates to accumulate within purge receptacle 22 to heights that extend into the region between sense plate 52 and excitation plate 54. This prevents false-positive detections of the extrudates when substantial volumes of the purged materials accumulate in purge receptacle 22.

As shown, sense plate 52, excitation plate 54, and reference plate 56 may extend from circuit board 50 in a substantially parallel manner. Suitable angles for sense plate 52, excitation plate 54, and reference plate 56 to each extend from circuit board 50 range from about 85 degrees to about 95 degrees, with particularly suitable angles ranging from about 88 degrees to about 92 degrees, and with even more particularly suitable angles including about 90 degrees.

Sense plate 52, excitation plate 54, and reference plate 56 each desirably has a length along the z-axis, a width along the y-axis, and a depth along the x-axis. Examples of suitable lengths for each of sense plate 52, excitation plate 54, and reference plate 56 range from about 1.3 centimeters (about 0.5 inches) to about 5.1 centimeters (about 2.0 inches), with particularly suitable lengths ranging from about 1.8 centimeters (about 0.7 inches) to about 3.3 centimeters (about 1.3 inches). Examples of suitable widths for each of sense plate 52, excitation plate 54, and reference plate 56 range from about 0.13 centimeters (about 0.05 inches) to about 1.3 centimeters (about 0.5 inches), with particularly suitable lengths ranging from about 0.3 centimeters (about 0.1 inches) to about 0.8 centimeters (about 0.3 inches).

Examples of suitable depths for each of sense plate 52, excitation plate 54, and reference plate 56 range from about 0.8 centimeter (about 0.3 inches) to about 5.1 centimeters (about 2.0 inches), with particularly suitable lengths ranging from about 1.3 centimeters (about 0.5 inches) to about 2.5 centimeters (about 1.0 inch). Correspondingly, suitable cross-sectional surface areas for each of sense plate 52, excitation plate 54, and reference plate 56 (based on lengths and depths) range from about 0.5 square-centimeters (about 0.2 square-inches) to about 10.2 square-centimeters (about 4.0 square-inches), with particularly suitable cross-sectional surface areas ranging from about 1.0 square-centimeter (about 0.4 square-inches) to about 3.3 square-centimeters (about 1.3 square-inches).

In one embodiment, sense plate 52, excitation plate 54, and reference plate 56 exhibit substantially the same dimensions. Additionally, the first and second gaps between excitation plate 54 and sense plate 52 and reference plate 56 are desirably about the same distance. Examples of suitable offset distances for excitation plate 54 from each of sense plate 52 and reference plate 56 range from about 0.3 centimeters (about 0.1 inches) to about 2.5 centimeters (about 1.0 inch), with particularly suitable offset distances ranging from about 0.5 centimeters (about 0.2 inches) to about 1.3 centimeters (about 0.5 inches).

While detector 12 is shown in use with conductive plates (i.e., sense plate 52, excitation plate 54, and reference plate 56), detector 12 may alternatively include a variety of different conductive components that function in the same manner as sense plate 52, excitation plate 54, and reference plate 56. As such, detector 12 may include a sense component, an excitation component, and a reference component, where the excitation component is configured to generate a first electrical field between the excitation component and the sense component, and to generate a second electrical field between the excitation component and the reference component.

ADC 58 is configured to sample and digitize capacitance signals from sense plate 52 and reference plate 56 over signal lines 64 and 66, respectively. The sampled signals may then be transmitted to processor 60, which is one or more microprocessors configured to analyze the received sampled signals and to communicate with controller 32 (shown in FIG. 1) over system interface 62 and communication line 40 (shown in FIG. 1). System interface 62 is an interface configured to communicate with controller 32 and/or other components of system 10. System interface 62 may also be configured to relay electrical power to excitation plate 54. In an alternative embodiment, one or more of ADC 58, processor 60, and system interface 62 may be located remotely from circuit board 50 (e.g., on a separate circuit board, not shown). In this embodiment, one or more of ADC 58, processor 60, and system interface may be located outside of build chamber 14 to reduce their exposure to the elevated temperature(s) within build chamber 14.

FIGS. 3 and 4 illustrate the process for detecting extrudates with the use of detector 12 during a liquefier purge. As discussed above, during a liquefier purge, controller 32 may direct gantry 18 to move extrusion head 20 in the horizontal x-y direction until extrusion head 20 is positioned over purge receptacle 22. In particular, as shown in FIG. 3, extrusion head 20 is desirably positioned such that the liquefier of extrusion head 20 that is to be purged (e.g., liquefier 20m) is substantially centered over the region between sense plate 52 and excitation plate 54 along the x-axis (shown in FIG. 1) and along the y-axis.

Power may also be supplied to excitation plate 54 to generate a first electrical field between sense plate 52 and excitation plate 54 (referred to as electrical field 68), and a second electrical field between excitation plate 54 and reference plate 56 (referred to as electrical field 70). ADC 58 may then calibrate detector 12. For example, ADC 58 may take one or more samples of the capacitance values of each of electrical fields 68 and 70 to attain a baseline value, such as pursuant to Equation 1:

$$\text{Baseline Value} = C_{EF1(i)} - C_{EF2(i)} \qquad \text{Equation 1}$$

where $C_{EF1(i)}$ is the capacitance value of electrical field 68 during the initial sampling, and $C_{EF2(i)}$ is the capacitance value of electrical field 70 during the initial sampling.

In the example shown in FIG. 3, only air resides within electrical fields 68 and 70. As such, the baseline value is substantially zero. However, as purge receptacle 22 accumulates extrudates on bottom floor 44 over multiple liquefier purges, the extrudates may begin to fill the region between sense plate 52 and excitation plate 54, thereby increasing the capacitance value $C_{EF1}$. This increase in the capacitance value is due to the relative static permittivities of the modeling and support materials (e.g., from about 2 to about 8 for thermoplastic materials), which are greater than the corresponding permittivity of air (i.e., 1.0). As such, when the accumulated extrudates displace portions of the air between sense plate 52 and excitation plate 54, the capacitance of electrical field 68 increases. As such determining the baseline value of Equation 1 allows processor 60 to effectively zero out the capacitance values of electrical field 68. As mentioned above, in addition to compensating for environmental changes, the dual-capacitor design prevents false-positive detections due to the accumulation of the extrudates in purge receptacle 22.

As shown in FIG. 4, extrusion head 20 may then extrude the modeling material from liquefier 20m for a set period of time. This produces extrudate 72, which passes between sense plate 52 and excitation plate 54, and increases the capacitance of electrical field 68. ADC 58 may then sample the capacitance values of electrical field 68 and transmit them to processor 60. Processor 60 desirably ignores the samples attained during an initial transition time period to allow extrudate 72 to reach electrical field 68. This prevents false-negative readings of a tip clog while extrudate 72 is initially traveling from liquefier 20m to electrical field 68. After the transition time expires, processor 60 may then compare the sampled capacitive values of electrical field 68 during the liquefier purge ($C_{EF1(p)}$) to a threshold value, such as pursuant to Equation 2:

$$C_{EF1(p)} - \text{Baseline Value} > \text{Threshold Value?} \qquad \text{Equation 2}$$

where the threshold value may vary depending on the expected change in capacitance due to the extrudates (e.g., extrudate 72). For example, the threshold value may be dependent on the diameter of extrudate 72 (e.g., from about 250 micrometers (about 10 mils) to about 510 micrometers (about 20 mils)), the composition of extrudate 72, the dimensions and locations of sense plate 52, excitation plate 54, and reference plate 56, and the like. Examples of suitable modeling and support materials for use with system 10 and detector 12 are discussed below.

In the current example, the baseline value is substantially zero and extrudate 72 causes $C_{EF1(p)}$ to be greater than the threshold value. As such, processor 60 determines that the conditions of Equation 2 are met, and, therefore, the presence of extrudate 72 is detected. As a result, the liquefier purge may be completed without alerting controller 32.

Alternatively, if a tip clog were present and extrudate 72 did not form, the $C_{EF1(p)}$ would not be greater than the threshold value. In this situation, processor 60 determines that the conditions of Equation 2 are not met and may transmit a signal to controller 32 that a loss of extrusion event has occurred. This allows controller 32 to then stop attempting to extrude the modeling material and to pause the build operation. Controller 32 may also display information to an operator of system 10 to inform the operator of the loss of extrusion event. As discussed above, the use of detector 12 in this manner allows tip clogging to be detected prior to forming a layer of 3D model 28 or support structure 30. This prevents an unsuccessful extrusion from occurring during the actual layer formation, thereby preserving the dimensional integrities of 3D model 28 and support structure 30.

Consumable Material Detector

Figure 5:
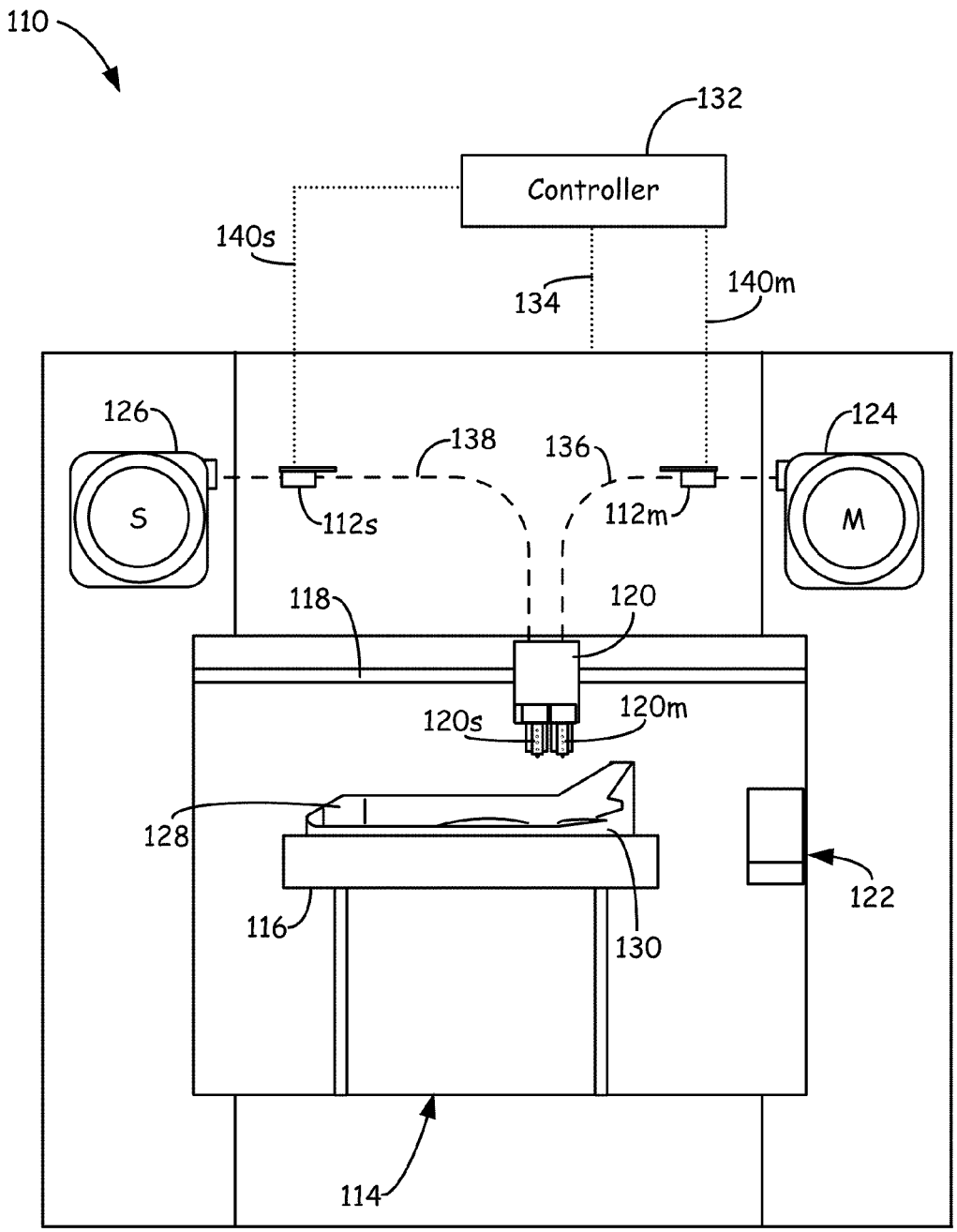
FIG. 5 is a schematic illustration of an extrusion-based digital manufacturing system that includes a capacitive detector of a second embodiment of the present disclosure.

FIG. 5 is a schematic illustration of system 110 in use with detectors 112m and 112s, which are alternatives to system 10 and detector 12, where the corresponding reference labels are increased by "100". Detectors 112m and 112s are capacitive detectors of the second embodiment of the present disclosure for detecting the presence of modeling and support materials fed to the extrusion head 120. In the shown embodiment, detector 112m is positioned along pathway 136 between supply source 124 and extrusion head 120, and detector 112s is positioned along pathway 138 between supply source 126 and extrusion head 120. In alternative embodiments, detector 112m may be positioned at a different location along pathway 136 between supply source 124 and extrusion head 120, and detector 112s may be positioned at a different location along pathway 138 between supply source 126 and extrusion head 120.

In one embodiment, detector 112m may be located adjacent to supply source 124, such as adjacent to the intersection of supply source 124 and pathway 136. Similarly, detector 112s may be located adjacent to supply source 126, such as adjacent to the intersection of supply source 126 and pathway 138. This embodiment allows detectors 112m and 112s to monitor the consumable materials (e.g., filaments of modeling and support materials) shortly after leaving supply sources 124 and 126, and is beneficial for detecting loss of extrusions events that occur within supply sources 124 and 126 and/or at the intersections with pathways 136 and 138.

For example, if a filament of the modeling material breaks within supply source 124 or is misfed to pathway 136, the filament will not reach detector 112m. Therefore, detector 112m will detect that the filament is not present in pathway 136, and may transmit signals to controller 132 over communication line 140m that a loss of extrusion event has occurred. This allows controller 132 to then stop attempting to feed the modeling material to extrusion head 120, and to pause the build operation. Controller 132 may also display information to an operator of system 110 to inform the operator of this loss of extrusion event.

In an alternative embodiment, detectors 112m and 112s may each be located adjacent to deposition head 120. For example, detectors 112m and 112s may be retained by gantry 118, or alternatively, may be positioned along pathways 136 and 138 at locations adjacent to gantry 118. This embodiment allows detectors 112m and 112s to monitor the consumable materials as they are being fed to extrusion head 120, and is beneficial for detecting loss of extrusions events that occur within pathways 136 and 138.

For example, if a filament of the modeling material breaks within pathway 136, the filament will not travel through detector 112m to extrusion head 120. Therefore, detector 112m will detect that the filament is not present in pathway 136, and may transmit signals to controller 132 over communication line 140m that a loss of extrusion event has occurred. This also allows controller 132 to then stop attempting to feed the modeling material to extrusion head 120, and to pause the build operation. Controller 132 may also display information to an operator of system 110 to inform the operator of this loss of extrusion event.

The locations of detectors 112m and 112s along pathways 136 and 138 contribute to the information relating to where the loss of extrusion event occurs. For example, if detector 112m is located adjacent to supply source 124, controller 132 may identify that the loss of extrusion event occurred at supply source 124. Alternatively, if detector 112m is located adjacent to extrusion head 120, controller 132 may only identify that the loss of extrusion occurred either at supply source 124 or somewhere along the feed route. As such, multiple detectors 112m may be used along pathway 136 to increase the accuracy of distinguishing where loss of extrusion events may occur along pathway 136.

For example, a first detector 112m may be located adjacent to supply source 124 and a second detector 112m may be located adjacent to extrusion head 120. A similar arrangement may also be applied to detector 112s and pathway 138 for monitoring loss of extrusion events along pathway 138. Moreover, these embodiments involving detectors 112m and 112s may also be used in combination with detector 12 (shown in FIGS. 1-4) retained in purge receptacle 122. This allows controller 132 to also distinguish a loss of extrusion event that occurs within extrusion head 120 (e.g., a clogged tip) from loss of extrusion events that occur within pathways 136 and 138.

Figure 6:
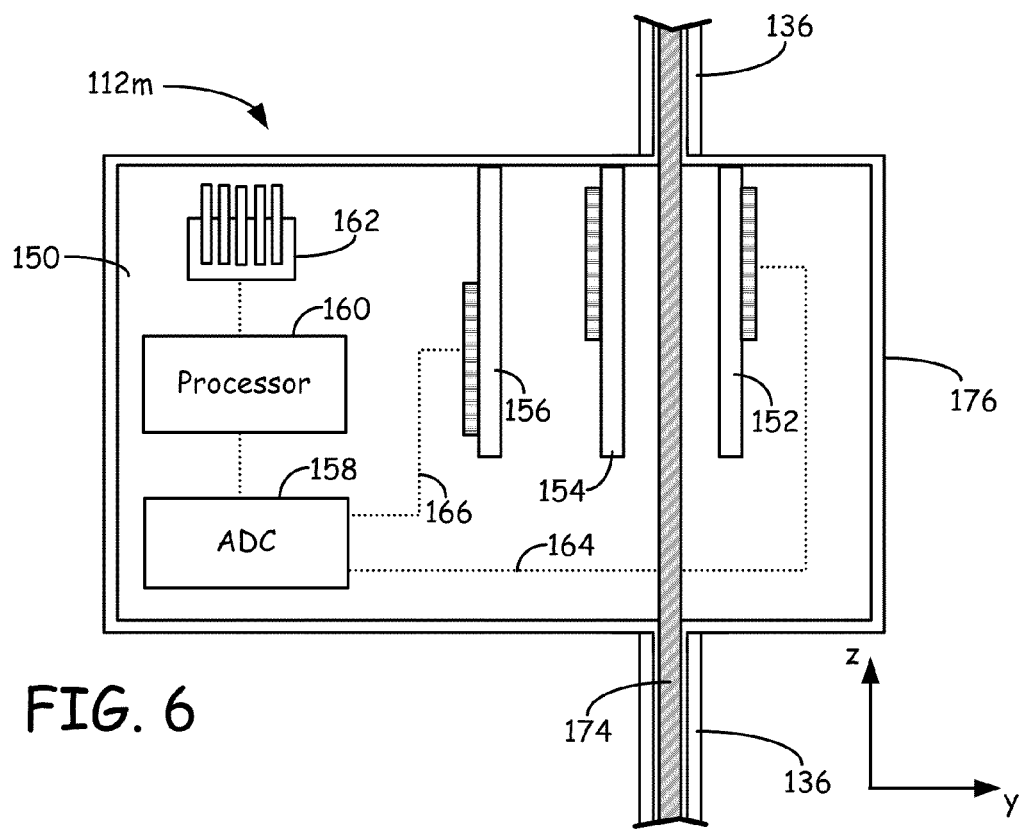
FIG. 6 is a side schematic illustration of the second embodied capacitive detector located adjacent to a pathway of a consumable material of the extrusion-based digital manufacturing system.

FIG. 6 is a schematic illustration of detector 112m in use with filament 174, where the following discussion of detector 112m also applies to detector 112s in the same manner. Detectors 112m and 112s may operate in a similar manner to that discussed above for detector 12. However, detectors 112m and 112s desirably operate continuously during a build operation to continuously monitor successive portions of the consumable materials (e.g., filament 174) as the consumable materials are fed to extrusion head 120. As shown in FIG. 6, detector 112m includes housing 176 that desirably engages with the guide tube of pathway 136 to provide a moisture barrier. Detector 112s may also include a similar housing (not shown) to provide a moisture barrier with pathway 138.

Figure 7:
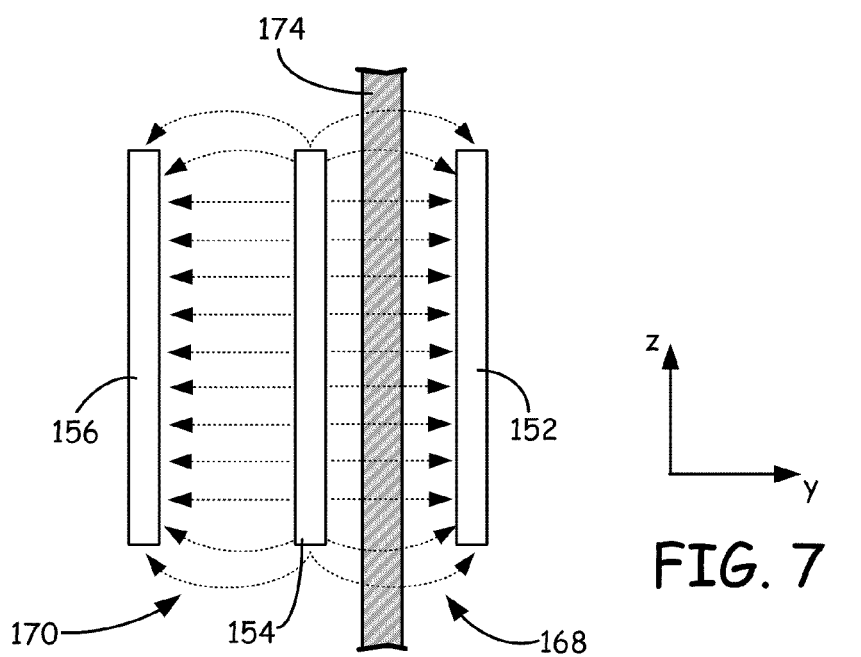
FIG. 7 is an expanded view of the second embodied capacitive detector, where a consumable material from a supply source is present.

As shown in FIG. 7, during a build operation, power may be supplied to excitation plate 154 to generate a first electrical field (referred to as electrical field 168) between sense plate 152 and excitation plate 154, and second electrical field (referred to as electrical field 170) between excitation plate 154 and reference plate 156. In this embodiment, however, ADC 158 may take one or more samples of the capacitance values of each of electrical fields 168 and 170 to determine whether a segment of filament 174 is currently located between sense plate 152 and excitation plate 154, such as pursuant to Equation 3:

$$C_{EF1(i)} - C_{EF2(i)} > \text{Threshold Value?} \qquad \text{Equation 3}$$

In this embodiment, the threshold value may also vary depending on the expected change in capacitance due to the consumable material (e.g., filament 174). For example, the threshold value may be dependent on the diameter of filament 174, the composition of filament 174, the dimensions and locations of sense plate 152, excitation plate 154, and reference plate 156, and the like.

Filament 174 may then be fed through pathway 136 to extrusion head 120, which causes filament 174 to pass between sense plate 152 and excitation plate 154. When filament 174 displaces a portion of the air between sense plate 152 and excitation plate 154, the capacitance of electrical field 168 increases. ADC 158 may then sample the capacitance values of electrical fields 168 and 170, and transmit them to processor 160. Processor 160 desirably ignores the samples attained during an initial transition time period to allow filament 174 to reach electrical field 168. This prevents false-negative readings of a loss of extrusion while filament 174 is traveling from supply source 124 to detector 112m.

In the current example, filament 174 causes the difference between the capacitance values of electrical fields 168 and 170 to exceed the threshold value. As such, processor 160 determines that the conditions of Equation 3 are met, and, therefore, the presence of filament 174 is detected. As a result, filament 174 may continue to be fed to extrusion head 170 without alerting controller 132.

Alternatively, if filament 174 is not residing between sense plate 152 and excitation plate 154 (e.g., due to a loss of extrusion event), then the difference between the capacitive values of electrical fields 168 and 170 is less than the threshold value. In this situation, processor 160 determines that the conditions of Equation 3 are not met and may transmit a signal to controller 132 that a loss of extrusion event has occurred. This allows controller 132 to then stop attempting to feed filament 174 to extrusion head 120, and may pause the build operation. Controller 132 may also display information to an operator of system 110 to inform the operator of the loss of extrusion event.

Comparing the capacitive values of electrical fields 168 and 170 allows detector 112m to compensate for environmental changes in pathway 136, such as changes in temperature and humidity levels. Additionally, this comparison allows consumable materials (e.g., filament 174) to be detected between sense plate 152 and excitation plate 154 regardless of the initial state of detector 112m. For example, in some situations, filament 174 may remain within pathway 136 and detector 112m after a build operation is complete, thereby allowing filament 174 to be readily available for use in a subsequent build operation. When the subsequent build operation is started and detector 112m is powered up, the difference in the capacitive values of electrical fields 168 and 170 allows processor 160 to identify that filament 174 is already present. As such, the use of reference plate 156 to generate electrical field 170 as a reference allows detector 112m to continuously monitor pathway 136 for consumable materials regardless of the initial state of detector 112m, while also compensating for environmental changes within pathway 136.

As discussed above, detectors 112m and 112s may also be used to determine one or more compositional properties of the modeling and support materials, such as moisture concentrations in the materials. For example, when determining the moisture concentration of filament 174, the predicted capacitance value of electrical field 168 may be computationally determined based on the volume of filament 174 within electrical field 168 (e.g., based on its diameter), the volume of air within electrical field 168, the dimensions and locations of sense plate 152, excitation plate 154, and reference plate 156, and the expected composition of the modeling material of filament 174.

As successive segments of filament 174 pass between sense plate 152 and excitation plate 154, processor 160 may compare the sampled capacitive values from sense plate 152 to the computationally determined values. The difference in the compared values may then be attributed to the concentration of water in the modeling material. Alternatively, if the composition and moisture content of filament 174 are known, the same process may be used to measure the diameters of successive segments of filament 174 as filament 174 passes through detector 112m.

Figure 8:
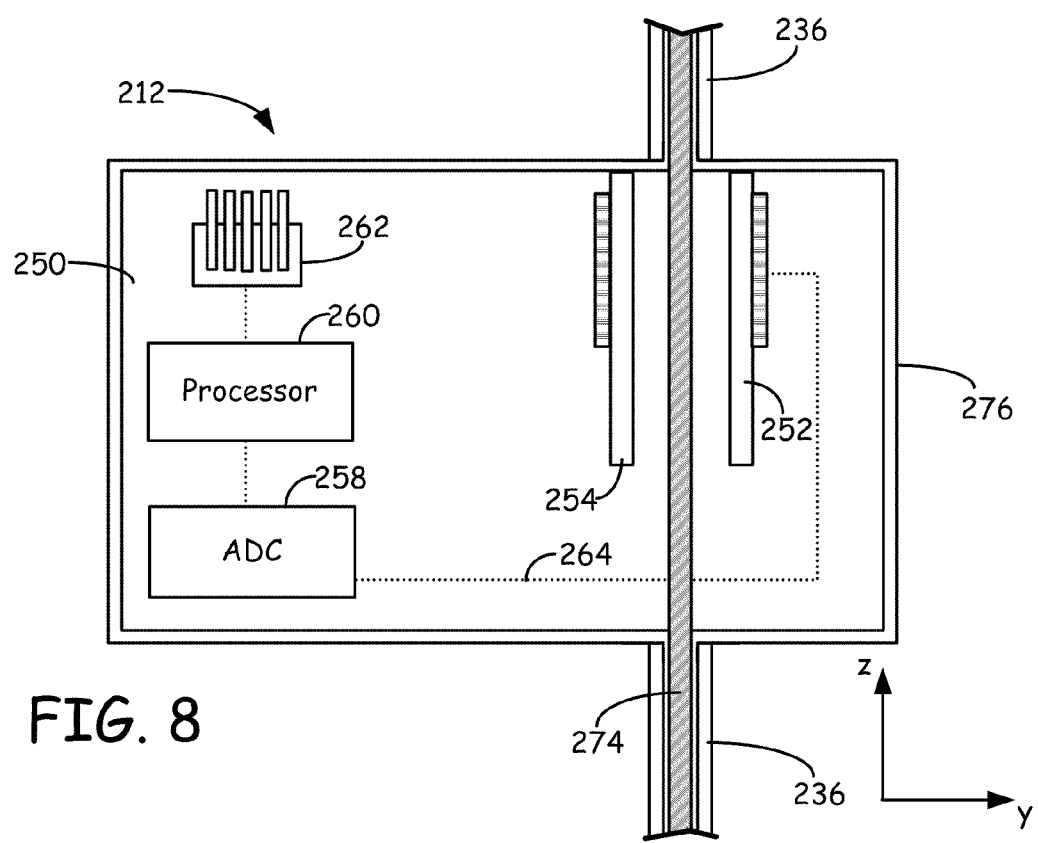
FIG. 8 is a side schematic illustration of a first alternative detector to the second embodied capacitive detector in use with a consumable material.

FIG. 8 is a schematic illustration of detector 212m in use with filament 274, where detector 212 is an alternative to detectors 112m and 112s (shown in FIGS. 5-7), where the corresponding reference labels are increased by "200" from detector 12 (shown in FIG. 1). As shown in FIG. 8, detector 212 is also a capacitive detector of the second embodiment of the present disclosure for detecting the presence of modeling and support materials fed to an extrusion head (not shown). In this embodiment, however, detector 212 only includes sense plate 252 and excitation plate 254, and a corresponding reference plate is omitted.

The omission of a reference plate reduces the capability of detector 212 to compensate for environmental changes. However, the presence of modeling and support materials may provide changes in capacitance values that are substantially greater than the variations that occur due to environmental changes.

Accordingly, in the current example, filament 274 causes the capacitance value of the electrical field generated between sense plate 252 and excitation plate 254 to exceed the threshold value. As such, processor 260 determines that the presence of filament 274 is detected. As a result, filament 274 may continue to be fed to extrusion head 270 without alerting the controller in the same manner as discussed above for detector 112m.

Alternatively, if filament 274 is not residing between sense plate 252 and excitation plate 254 (e.g., due to a loss of extrusion event), then the capacitive value of electrical field between sense plate 252 and excitation plate 254 is less than the threshold value. In this situation, processor 260 determines may transmit a signal to the controller that a loss of extrusion event has occurred, in the same manner as discussed above for detector 112m. Thus detector 212 provides a suitable alternative to detectors 112m and 112s for detecting the presence of modeling and support materials fed to an extrusion head.

Figure 9:
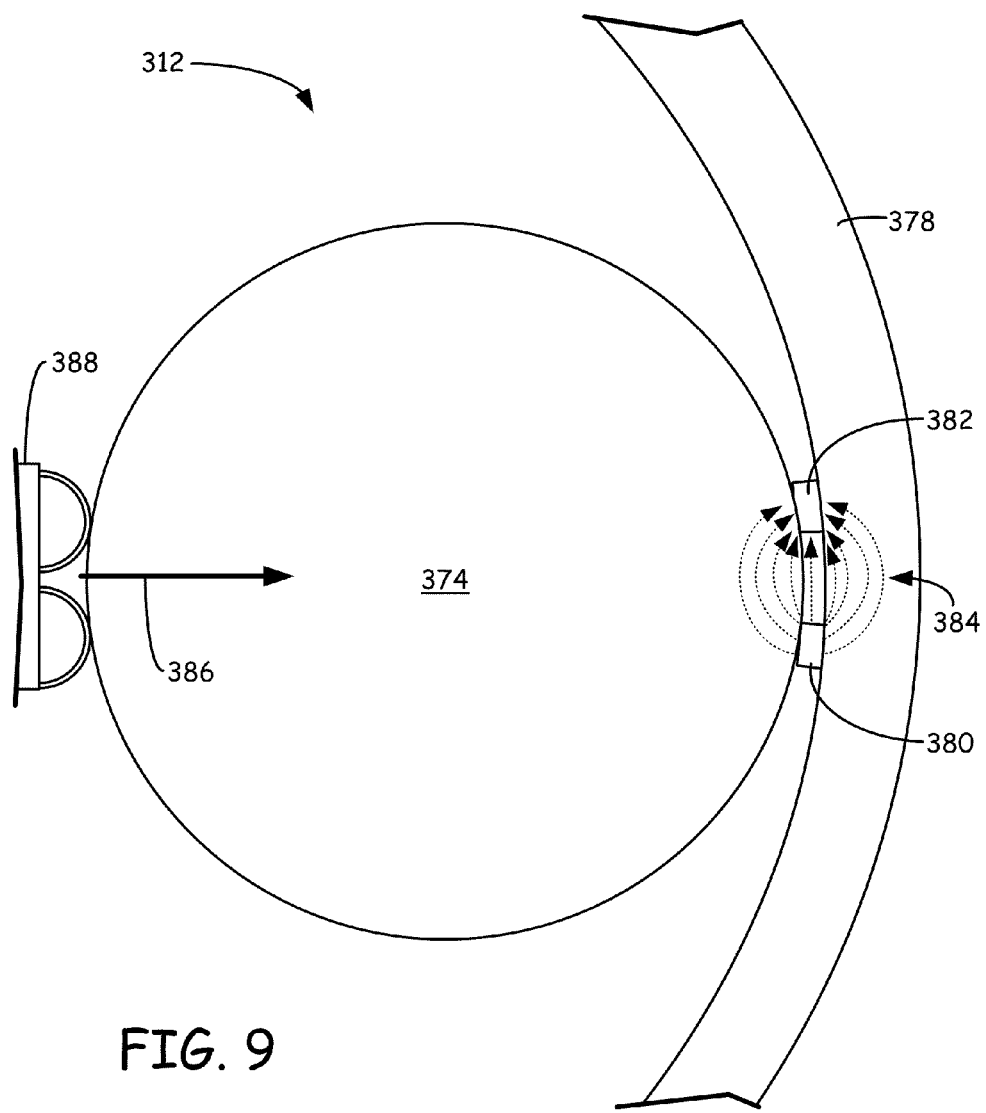
FIG. 9 is a top view of a second alternative detector to the second embodied capacitive detector in use with a consumable material.

FIG. 9 is a top view of detector 312 in use with filament 374, where detector 312 is an alternative to detector 12 (shown in FIGS. 1-4), detectors 112m and 112s (shown in FIGS. 5-7), and detector 212 (shown in FIG. 8), where the corresponding reference labels are increased by "300" from detector 12. Detector 312 is also a capacitive detector of the second embodiment of the present disclosure for detecting the presence of modeling and support materials fed to an extrusion head (not shown). In this embodiment, detector 312 includes flexible circuit 378, sense trace 380, and excitation trace 382.

Flexible circuit 378 is a thin-film circuit (e.g., a polyimide film circuit) that retains sense trace 380 and excitation trace 382, and may be connected to a circuit board corresponding to circuit board 150 (shown in FIG. 6). As shown, flexible circuit 378 has a film thickness generally extending along the y-axis. Examples of suitable average film thicknesses for flexible circuit 378 range from about 130 micrometers (about 5 mils) to about 380 micrometers (about 15 mils).

Sense trace 380 and excitation trace 382 are conductive components (e.g., copper traces) that may be used in lieu of sense plate 152 and excitation plate 154 (shown in FIGS. 6 and 7). In an alternative embodiment, detector 312 may also include an additional conductive component to function as a reference component in the same manner as reference plate 156 (shown in FIGS. 6 and 7). As shown, sense trace 380 and excitation trace 382 each has a width generally along the x-axis. Examples of suitable average widths for each of sense trace 380 and excitation trace 382 range from about 25 micrometers (about 1 mil) to about 130 micrometers (about 5 mils), with particularly suitable average widths ranging from about 50 micrometers (about 2 mils) to about 100 micrometers (about 4 mils). Examples of suitable offset distances between sense trace 380 and excitation trace 382 range from about 50 micrometers (about 2 mils) to about 250 micrometers (about 10 mils), with particularly suitable offset distances ranging from about 100 micrometers (about 4 mils) to about 200 micrometers (about 8 mils).

As shown in FIG. 9, power supplied to excitation trace 382 generates electrical field 384, which functions as a fringing electrical field that may extend beyond sense trace 380 and excitation trace 382 into filament 374 by about 130 micrometers (about 5 mils). During operation, filament 374 is desirably biased in the direction of arrow 386 toward sense trace 380 and excitation trace 382 with biasing component 388 (e.g., a clip spring). The bias desirably maintains contact between filament 374 and sense trace 380 and excitation trace 382, while also desirably minimizing undue sliding friction.

This arrangement allows detector 312 to monitor compositional properties of filament 374 as successive segments of filament 374 pass through detector 312 in a manner that is independent of the diameter of filament 374. Accordingly, if the expected composition of filament is known (e.g., the expected composition of the modeling or support material), the concentrations of water in successive segments of filament 374 may be determined based on the sampled capacitive values, as discussed above. This embodiment is beneficial for use with consumable materials (e.g., filament 374) having dimensions that may vary over the lengths of the consumable materials (e.g., diameters that vary over the lengths).

The above discussions of the capacitive detectors of the present disclosure (e.g., detectors 12, 112m, 112s, 212, and 312) are directed to their use in detecting loss of extrusion events in extrusion-based digital manufacturing systems (e.g., systems 10 and 110), detecting compositional properties of the consumable materials, and the like. However, the capacitive detectors of the present disclosure may also be used to detect the presence of consumable materials and/or extrudates during a variety of system functions. For example, detectors 12, 112m, 112s, 212, and 312 may also be used to detect the presence of a consumable material while the consumable material is loaded to systems 10 and 110, such as during automated material loading processes that may occur prior to an actual build operation.

Consumable Materials

The capacitive detectors of the present disclosure (e.g., detectors 12, 112m, 112s, 212, and 312) may be used with a variety of different consumable materials (e.g., modeling and support materials). As discussed above, in one embodiment, the consumable materials may be provided as filaments. In embodiments in which the filaments are cylindrical, examples of suitable average diameters for the filaments range from about 0.8 millimeters (about 0.03 inches) to about 2.5 millimeters (about 0.10 inches), with particularly suitable average diameters ranging from about 1.0 millimeter (about 0.04 inches) to about 2.3 millimeters (about 0.09 inches), and with even more particularly suitable average diameters ranging from about 1.3 millimeters (about 0.05 inches) to about 2.0 millimeters (about 0.08 inches). On embodiments in which the filaments are non-cylindrical, suitable dimensions and designs for the non-cylindrical filaments include those disclosed in Batchelder et al., U.S. patent application Ser. No. 12/612,333.

The consumable materials may include a variety of extrudable modeling and support materials for respectively building 3D model 28 and support structure 30. Suitable modeling materials for use with systems 10 and 110 include polymeric and metallic materials. In some embodiments, suitable modeling materials include materials having amorphous properties, such as thermoplastic materials, amorphous metallic materials, and combinations thereof. Examples of suitable thermoplastic materials for the consumable materials include acrylonitrile-butadiene-styrene (ABS) copolymers, polycarbonates, polysulfones, polyethersulfones, polyphenylsulfones, polyetherimides, amorphous polyamides, modified variations thereof (e.g., ABS-M30 copolymers), polystyrene, and blends thereof. Examples of suitable amorphous metallic materials include those disclosed in Batchelder, U.S. Patent Application Publication No. 2009/0263582.

Suitable support materials for use with systems 10 and 110 include polymeric materials. In some embodiments, suitable support materials include materials having amorphous properties (e.g., thermoplastic materials) and that are desirably removable from the corresponding modeling materials after 3D model 28 and support structure 30 are built. Examples of suitable support materials for the consumable materials include water-soluble support materials commercially available under the trade designations "WATERWORKS" and "SOLUBLE SUPPORTS" from Stratasys, Inc., Eden Prairie, Minn.; break-away support materials commercially available under the trade designation "BASS" from Stratasys, Inc., Eden Prairie, Minn., and those disclosed in Crump et al., U.S. Pat. No. 5,503,785; Lombardi et al., U.S. Pat. Nos. 6,070,107 and 6,228,923; Priedeman et al., U.S. Pat. No. 6,790,403; and Hopkins et al., U.S. patent application Ser. No. 12/508,725.

The compositions of the modeling and support materials may also include additional additives, such as plasticizers, rheology modifiers, inert fillers, colorants, stabilizers, and combinations thereof. Examples of suitable additional plasticizers for use in the support material include dialkyl phthalates, cycloalkyl phthalates, benzyl and aryl phthalates, alkoxy phthalates, alkyl/aryl phosphates, polyglycol esters, adipate esters, citrate esters, esters of glycerin, and combinations thereof. Examples of suitable inert fillers include calcium carbonate, magnesium carbonate, glass spheres, graphite, carbon black, carbon fiber, glass fiber, talc, wollastonite, mica, alumina, silica, kaolin, silicon carbide, composite materials (e.g., spherical and filamentary composite materials), and combinations thereof. In embodiments in which the composition includes additional additives, examples of suitable combined concentrations of the additional additives in the composition range from about 1% by weight to about 10% by weight, with particularly suitable concentrations ranging from about 1% by weight to about 5% by weight, based on the entire weight of the composition.

EXAMPLES

The present disclosure is more particularly described in the following examples that are intended as illustrations only, since numerous modifications and variations within the scope of the present disclosure will be apparent to those skilled in the art. Unless otherwise noted, all parts, percentages, and ratios reported in the following examples are on a weight basis, and all reagents used in the examples were obtained, or are available, from the chemical suppliers described below, or may be synthesized by conventional techniques.

Liquefier purge tests were performed with a capacitive detector corresponding to detector 12 (shown in FIGS. 1-4) to determine the effectiveness of the capacitive detector in detecting the presence and absence of extrudates. The capacitive detector was mounted in a purge receptacle of an extrusion-based digital manufacturing system commercially available under the trade designation "DIMENSION uPRINT" Personal 3D Printer from Stratasys, Inc., Eden Prairie, Minn. More than 10,000 liquefier purges were then performed after filaments of modeling and support materials were auto-loaded and extrusion head togglings were performed.

Figure 10:
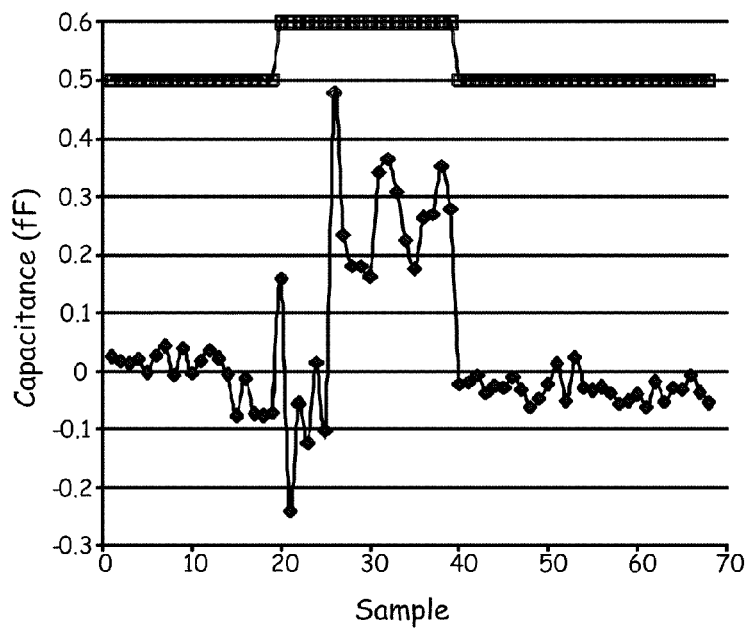
FIG. 10 is graphical illustration of a liquefier purge test performed with a capacitive detector corresponding to the first embodied capacitive detector and a modeling material.
Figure 11:
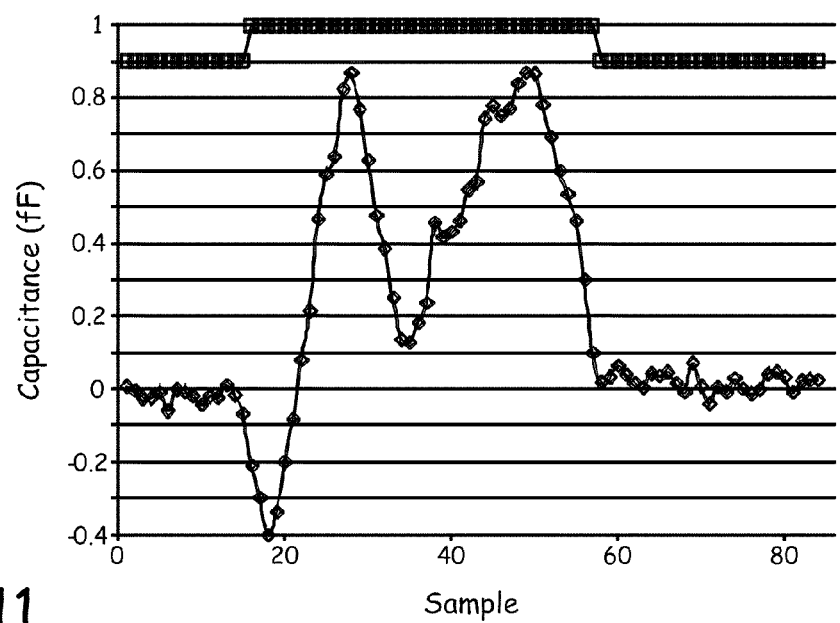
FIG. 11 is graphical illustration of a liquefier purge test performed with the capacitive detector and a support material.

FIGS. 10 and 11 are graphical illustrations of two of the liquefier purge tests performed, where the results shown in FIG. 10 were obtained by purging an ABS modeling material commercially available from Stratasys, Inc., Eden Prairie, Minn., and the results shown in FIG. 11 were obtained by purging a soluble support modeling material commercially available under the trade designation "WATERWORKS" from Stratasys, Inc., Eden Prairie, Minn. As shown in FIGS. 10 and 11, when the extrudates each reached the detector, the capacitance values exceeded the threshold value, thereby triggering response signals (shown as the top plots in FIGS. 10 and 11).

During a portion of the tested liquefier purges, loss of extrusion events were intentionally induced to see whether the capacitive detector was capable of detecting loss of extrusion events. Throughout the more than 10,000 liquefier purges, the capacitive detector detected the presence of the extrudates 100% of the time when the extrudates were present, and detected a loss of extrusion event 100% of the time when the events were induced (i.e., when the extrudates were absent).

Figure 12:
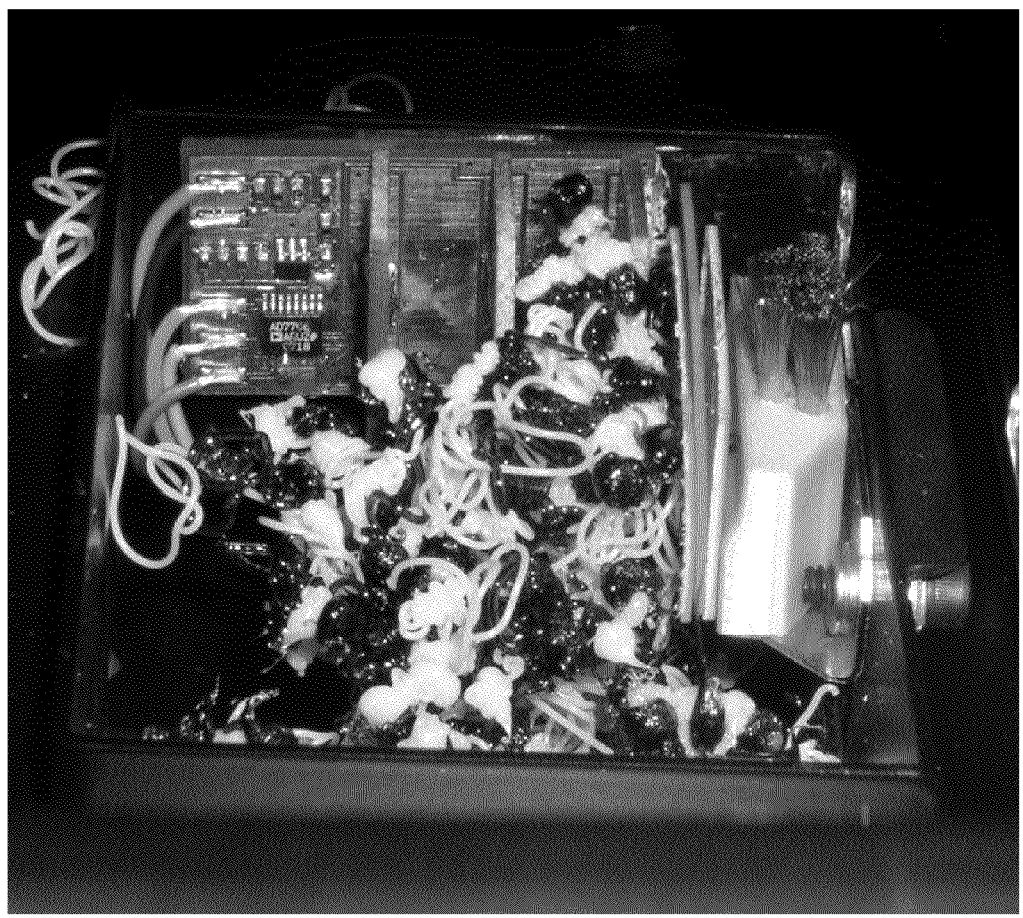
FIG. 12 is a photograph of a purge receptacle of an extrusion-based digital manufacturing system and the capacitive detector used in the liquefier purge tests, illustrating an accumulation of modeling and support material extrudates.

FIG. 12 is a photograph of the capacitive detector used in the liquefier purge tests, where the capacitive detector was retained in the purge receptacle with a tip wipe assembly (mounted at the right-most side of the purge receptacle shown in FIG. 12). As shown, the extrudates of the modeling and support materials substantially filled the region between the sense plate and the excitation plate (the right-most plates shown in FIG. 12). Even with this fill volume, the capacitive detector was capable of detecting the presence of additional extrudates 100% of the time when the additional extrudates were present. As discussed above, this is attainable with the use of the reference plate (the left-most plate shown in FIG. 12) to generate a second electrical field that functions as a baseline reference. Accordingly, the capacitive detector provided an effective means for detecting loss of extrusion events (e.g., tip clogging) in the extrusion-based digital manufacturing system.

Although the present disclosure has been described with reference to preferred embodiments, workers skilled in the art will recognize that changes may be made in form and detail without departing from the spirit and scope of the disclosure.

The invention claimed is:

1. A detector for use in an extrusion-based digital manufacturing system, the detector comprising:
    a control board configured to be retained in the extrusion-based digital manufacturing system;
    a sense conductive component operably secured to the control board;
    an excitation conductive component operably secured to the control board to define a first gap between the sense conductive component and the excitation conductive component, the first gap being configured to receive a consumable material used in the extrusion-based digital manufacturing system, wherein the excitation conductive component is configured to generate a first electrical field across the first gap; and
    a reference conductive component operably secured to the control board on an opposing side of the excitation conductive component from the sense conductive component to define a second gap between the excitation conductive component and the reference component, wherein the excitation conductive component is further configured to generate a second electrical field across the second gap.

2. The detector of claim 1, wherein the control board is configured to be operably mounted to a purge receptacle of the extrusion-based digital manufacturing system, and wherein the consumable material comprises an extrudate from an extrusion head of the extrusion-based digital manufacturing system.

3. The detector of claim 1, wherein the control board is configured to communicate with a controller of the extrusion-based digital manufacturing system.

4. The detector of claim 1, wherein the control board is operably mounted adjacent to a pathway of the consumable material between a supply source of the consumable material and an extrusion head of the extrusion-based digital manufacturing system.

5. The detector of claim 1, wherein the excitation conductive component is offset from the sense conductive component by an offset distance ranging from about 0.3 centimeters to about 2.5 centimeters.

6. The detector of claim 1, wherein the sense conductive component and the excitation conductive component each have a surface area ranging from about 0.2 square-centimeters to about 4.0 square-centimeters.

7. The detector of claim 1, wherein the consumable material used in the extrusion-based digital manufacturing system has a filament geometry and a composition that comprises a thermoplastic material.

8. A detector for use in an extrusion-based digital manufacturing system, the detector comprising:
    a control board configured to be retained in the extrusion-based digital manufacturing system;
    an excitation conductive component operably secured to the control board;
    a sense conductive component operably secured to the control board;
    a reference conductive component operably secured to the control board on an opposing side of the excitation conductive component from the sense conductive component to define a gap between the excitation conductive component and the reference component;
    a biasing component configured to engage a consumable material with the excitation conductive component and the reference conductive component, wherein the excitation conductive component is configured to generate an electrical field with the sense conductive component; and
    a processor operably secured to the control board and configured to compare capacitive values of sampled signals operably received from the sense conductive component to predetermined capacitive values to identify at least one compositional property of the consumable material.

9. The detector of claim 8, wherein the control board is configured to communicate with a controller of the extrusion-based digital manufacturing system.

10. The detector of claim 8, wherein the control board is operably mounted adjacent to a pathway of the consumable material between a supply source of the consumable material and an extrusion head of the extrusion-based digital manufacturing system.

11. The detector of claim 8, wherein the excitation conductive component is offset from the sense conductive component by an offset distance ranging from about 50 micrometers to about 250 micrometers.

12. The detector of claim 8, wherein the at least one compositional property comprises a moisture concentration in the consumable material.

13. A method for detecting a consumable material in an extrusion-based digital manufacturing system, the method comprising:
- generating a first electrical field between an excitation conductive component and a sense conductive component;
- generating a second electrical field between the excitation conductive component and a reference conductive component;
- introducing the consumable material between the excitation conductive component and the sense conductive component of the extrusion based digital manufacturing system while the first and second electrical fields are generated;
- sampling capacitive values of the first and second electrical fields while the consumable material is introduced between the excitation conductive component and the sense conductive component; and
- performing at least one computational analysis on the sampled capacitive values to identify the presence of the consumable material between the excitation conductive component and the sense conductive component.

14. The method of claim 13, wherein the excitation conductive component, the sense conductive component, and the reference conductive component are operably mounted to a purge receptacle of the extrusion-based digital manufacturing system, and wherein the consumable material comprises an extrudate from an extrusion head of the extrusion-based digital manufacturing system.

15. The method of claim 13, wherein the excitation conductive component, the sense conductive component, and the reference conductive component are operably mounted adjacent to a pathway of the consumable material between a supply source of the consumable material and an extrusion head of the extrusion-based digital manufacturing system.

16. The method of claim 13, wherein performing the at least one computational analysis comprises determining differences between the sampled capacitive values.

17. The method of claim 13, and further comprising determining a baseline value based on differences between the sampled capacitive values, wherein the computational analysis is further based on the baseline value.

18. The method of claim 13, and further comprising communicating with a controller of the extrusion-based digital manufacturing system based at least in part on the at least one performed computational comparison.

19. The method of claim 18, wherein communicating with the controller comprises transmitting at least one signal to the controller relating to a loss of extrusion event.

* * * * *